US011199163B2

(12) United States Patent
Yamamoto et al.

(10) Patent No.: US 11,199,163 B2
(45) Date of Patent: Dec. 14, 2021

(54) ELECTRON GENERATION MEANS, COMBUSTION PROMOTING MEANS, MOVING BODY, AND STERILIZATION/DEODORIZATION MEANS

(71) Applicant: KABUSHIKI KAISHA Global Tec Corporation, Miyazaki (JP)

(72) Inventors: Kazunori Yamamoto, Miyazaki (JP); Tokuzou Yamamoto, Miyazaki (JP)

(73) Assignee: KABUSHIKI KAISHA Global Tec Corporation, Miyazaki (JP)

( * ) Notice: Subject to any disclaimer, the term of this patent is extended or adjusted under 35 U.S.C. 154(b) by 0 days.

(21) Appl. No.: 17/059,471

(22) PCT Filed: Jan. 28, 2019

(86) PCT No.: PCT/JP2019/002668
§ 371 (c)(1),
(2) Date: Nov. 30, 2020

(87) PCT Pub. No.: WO2020/157791
PCT Pub. Date: Aug. 6, 2020

(65) Prior Publication Data
US 2021/0222651 A1    Jul. 22, 2021

(51) Int. Cl.
*B62D 35/00* (2006.01)
*B62D 37/02* (2006.01)
(Continued)

(52) U.S. Cl.
CPC ............... *F02M 27/04* (2013.01); *A61L 9/16* (2013.01); *B62D 35/00* (2013.01); *B62D 37/02* (2013.01); *H02M 7/04* (2013.01)

(58) Field of Classification Search
CPC ..... A61L 9/16; B62D 35/00–02; B62D 37/02; F02M 27/04; H02M 7/04; H02M 7/05
See application file for complete search history.

(56) References Cited

U.S. PATENT DOCUMENTS 5,725,151 A * 3/1998 Hetrick ................. B05B 5/0533
                                                          239/3
6,167,872 B1 * 1/2001 Campagna .............. F02B 51/04
                                                          123/538
(Continued)

FOREIGN PATENT DOCUMENTS

JP     2003-293900     10/2003
JP     2005-090338     4/2005
(Continued)

OTHER PUBLICATIONS

Tottori, Kotaro, "Studies on Static Electrification of Non-conductive Liquid (second report) Effect of Non-conductive Liquid on Receiver Tank (p. 25 to 27)" Toyama University Academic Information Repository URL<https://toyama.repo.nii.ac.jp/?action=repository_uri&item_id=3773 &file_id=18&file_no=1> (w/ partilal machine translation).

(Continued)

*Primary Examiner* — Gregory A Blankenship
(74) *Attorney, Agent, or Firm* — Mori & Ward, LLP

(57) ABSTRACT

An electron generation means for generating electrons includes a rectifier circuit and a booster circuit. AC power from a power supply is passed through the rectifier circuit in advance and then flown to the booster circuit. The rectifier circuit, according to the plus/minus inversion cycle of the said AC power, blocks current flowing toward a second terminal in a state where a first terminal of the rectifier circuit has a positive potential, and current flows from the second terminal only in the state where the first terminal of the rectifier circuit has a negative potential, and thus current flows only in one direction of the alternating current. The booster circuit boosts the voltage on a primary side, and electrons are generated from one terminal on a secondary (Continued)

side of the booster circuit only in a state where the first terminal of the rectifier circuit has a negative potential.

13 Claims, 6 Drawing Sheets

(51) Int. Cl.
  *A61L 9/16* (2006.01)
  *H02M 7/04* (2006.01)
  *F02M 27/04* (2006.01)

(56) References Cited

U.S. PATENT DOCUMENTS

| | | | |
|---|---|---|---|
| 6,202,633 B1* | 3/2001 | Campagna | F02M 27/04 123/536 |
| 6,675,780 B1* | 1/2004 | Wendels | F02M 27/04 123/536 |
| 2008/0122252 A1* | 5/2008 | Corke | H05H 1/2406 296/180.2 |
| 2012/0152198 A1* | 6/2012 | Kim | B62D 35/005 123/188.1 |
| 2013/0188407 A1* | 7/2013 | Uguen | H05B 45/385 363/126 |
| 2016/0094142 A1* | 3/2016 | Mahdavikhah | H02M 1/12 363/44 |
| 2016/0264192 A1 | 9/2016 | Tanahashi et al. | |
| 2016/0280162 A1 | 9/2016 | Yamada et al. | |
| 2017/0279367 A1* | 9/2017 | Qiu | G05B 11/42 |
| 2018/0038322 A1* | 2/2018 | Karl | F02D 41/1441 |
| 2019/0191633 A1 | 6/2019 | Yamamoto | |
| 2019/0342985 A1* | 11/2019 | Dadheech | H05H 1/2481 |
| 2021/0088010 A1* | 3/2021 | Cabauatan | F02M 27/04 |
| 2021/0222651 A1* | 7/2021 | Yamamoto | B62D 37/02 |
| 2021/0296981 A1* | 9/2021 | Neudorf | G01R 19/16538 |

FOREIGN PATENT DOCUMENTS

| | | |
|---|---|---|
| JP | 2008-038618 | 2/2008 |
| JP | 2008-295937 | 12/2008 |
| JP | 2009-247200 | 10/2009 |
| JP | 50-42660 | 10/2012 |
| JP | WO2015/064195 | 5/2015 |
| JP | 2016-168951 | 9/2016 |
| JP | 2018-141397 | 9/2018 |
| JP | 2018-161026 | 10/2018 |

OTHER PUBLICATIONS

Technical Data of Japan Petroleum Energy Center, General Incorporated Foundation, URL<http://www.pecl.or.jp/japanese/safer/knowledge/doc/no-75.doc> (w/ partital machine translation).

International Search Report for corresponding International Application No. PCT/JP2019/002668, dated May 7, 2019.

Written Opinion for corresponding International Application No. PCT/JP2019/002668, dated May 7, 2019.

* cited by examiner

ELECTRON GENERATION MEANS, COMBUSTION PROMOTING MEANS, MOVING BODY, AND STERILIZATION/DEODORIZATION MEANS

TECHNICAL FIELD

The present invention relates to an electron generation means capable of generating electrons in a stable state even with small power consumption. More in detail, the present invention relates to combustion promoting means, which generates electrons in a stable state with a circuit not easily damaged and promotes combustion by instantaneously gasifying fine particles of fuel injected into an internal combustion engine.

Furthermore, the present invention relates to a moving body provided with an electron generation means, specifically relates to a moving body which reduces static electricity generated by friction between the moving body and air during movement. Further, the present invention relates to a sterilizing/deodorizing means, which sterilizes and deodorizes bacteria which causes an offensive odor by the liquid charged with electrons generated by the electron generation means.

BACKGROUND ART

It has been conventionally known that vaporizing fuel in a short time is preferable to improve the combustion efficiency of the fuel burned in an internal combustion engine. A revolution number of an engine means a revolution number of crankshafts per minute, and can be several thousand revolutions at maximum for an average passenger car. That is, in the case of a 4-stroke engine, the combustion process repeats 1000 cycles or more in a minute. Therefore, to improve combustion efficiency, it is preferable to vaporize fuel in a short time.

In Non-Patent Document 1, it is shown that gasoline supplied from a plurality of oil refining companies flows into a receiver tank in an insulated state from a hose of a metering device of a commercial gas station, and the charging tendency of the gasoline becomes positive charge (refer to page 25, line 18 to 29 and page 26, FIG. 18). Further, in Non-Patent Document 2, it is shown that oil, which is a dielectric material, is easily charged to positive with a flow, stirring, etc. (Non-Patent Document 2, Technical Documents page 5-1 to 5-3).

Static electricity is generated when the object which has emitted the electrons is in the state of being biased to positive charge by transferring electrons from one object to another when dissimilar objects in contact with each other are rubbed and separated, and the charge bias is eliminated by combining electrons with the positive charge (hereinafter, referred to as neutralization). The charging phenomenon of an object by static electricity is classified into surface charge generated on metal or the like and space charge generated on dielectric such as refined oil.

As for the surface charge, the charge exists only on the object surface, and the charge does not exist inside. The surface charge is easily removed by grounding the object to the earth. Grounding an electric device is intended to remove this surface charge (Non-Patent Document 1, page 27, line 5 to 7).

On the other hand, as for the space charge, the charge caused by the charging phenomenon is not limited to the object surface but exists inside the object. When an object with space charge and the earth are grounded, the charge is gradually reduced by repulsive force between the charges or neutralization, but it tends to be difficult to remove rapidly (Non-Patent Document 1, page 27, line 7 to 11).

Not only solid material but also even liquid or mist-like diffused objects generate static electricity at the time of a collision, friction, peeling, and the like. Substances with small electric conductivity, such as naphtha, kerosene, gasoline, light oil, or the like in refined oils, are said to be likely to accumulate static electricity (Non-Patent Document 2, page 5-1 line 3 to 5). Therefore, even in the case of fuel oil not electrostatically charged while stored in a fuel tank, static electricity appears by friction with the metal pipe when pumped by the pump. In this instance, since the metal is more likely to be negatively charged than the fuel oil, the metal pipe is negatively charged, and the fuel oil is positively charged.

The charge of the metal pipe is a surface charge. In the case of a vehicle, since metal components are conducting indirectly to the negative terminal of the battery, the surface charge of negative charge is easily neutralized. On the other hand, since the fuel oil is space-charged, the positive charge on the surface is neutralized, but the positive charge still exists inside (Non-Patent Document 1, page 27, line 30 to 32). With this, even when sprayed from the fuel injection device into the fuel combustion space, it is in the positively-charged state. Conventionally, focusing on this charging phenomenon of fuel, technologies of promoting combustion of fuel particles have been disclosed, in which internal combustion engines or fuel particles are electrically charged by supplying electric charge from the outside.

Patent Document 1 discloses a technology of a fuel injection device for an internal combustion engine, which charges fuel by corona discharge and atomizes the fuel with small power consumption. The conventional technology has a problem that applying high voltage is necessary to charge the fuel by corona discharge. According to the technology described in Patent Document 1, the corona discharge is effectively generated by increasing the charge amount at a portion where charged particles are irradiated by providing the electric resistance increasing portion which increases electric resistance to the portion of the charging electrode where the charged particles are irradiated.

Specifically, positive charges are irradiated to the piston's surface from the charge irradiation pin and charge the piston's surface to a positive charge. Fine particles of the injected fuel are provided with a positive charge from the fuel charging pin incorporated around the fuel injection part. Since the piston surface and the fine fuel particles are charged with a positive charge, the repulsion due to the electrostatic repulsion atomizes the fuel in the fuel combustion space and promotes the combustion of the fuel.

In Patent Document 2, a technology of an internal combustion engine is disclosed, which improves combustion by supplying negative ions to the fuel combustion space. According to the technology described in Patent Document 2, at least a part of the wall surface forming the fuel combustion space is covered with piezoelectric elements. The said piezoelectric elements made of tourmaline or the like generate static electricity during the period when the pressure inside the fuel combustion space increases due to the pressure for compressing the air-fuel mixture or the increased pressure with the combustion of the air-fuel mixture. With the generation of static electricity, negative ions are generated around the piezoelectric elements, and the negative ions are supplied to the fuel combustion space at a low cost.

In Patent Document 3, a technology is disclosed, which destaticizes positive charge by discharging the positive charge from a vehicle that is positively charged by static electricity generated by traveling. According to the technology described in this Document, a conductive film is attached to a flow-separating portion, where positively-charged airflow flowing around the vehicle body during traveling starts to change to the flow separated from the surface of the vehicle body. It says that it is preferable to provide the conductive film with a pointed portion that easily induces self-discharge.

The place where the conductive film is attached is less likely to be positively charged, and the separation of airflow from the vehicle body surface is suppressed. Then, air turbulence and air pressure fluctuations at and around a specific portion on the surface of the vehicle body are suppressed. As a result, it says that driving characteristics such as power performance, steering stability, braking performance, or riding comfort are improved from extremely low-speed driving to high-speed driving.

Patent Document 4 discloses a technology of an electron dissipating device by the inventor of the present application. According to the technology described in Patent Document 4, electrons generated by the electron dissipating device are dissipated from the dissipative end of the electric wire to improve the fuel efficiency of vehicles, ships, and the like. Specifically, it is disclosed that the electron dissipative end is immersed in a diesel engine's fuel tank to supply electrons to the fuel to improve fuel efficiency.

However, to generate electrons in the fuel tank, the fuel tank itself needs to be modified. Then, the applicable vehicles are limited, and it cannot be applied to many vehicles, including used vehicles. Therefore, the inventor of the present application earnestly studied the combustion improving means with a stable circuit, which can be easily applied not only to new vehicles but also to used vehicles without changing the vehicles' driving mechanism and contemplated toward the present invention.

The electron dissipating device described in Patent Document 4 is an electron generation device that does not generate ozone. Specifically, to generate only electrons from the secondary side of the booster circuit, one end of the secondary side circuit of the booster circuit is connected to the primary-side circuit; between the other end of the secondary side circuit and the electron dissipative end, a diode for interrupting a current flowing from the said other end to the said electron dissipative end was provided. When applying to a vehicle, the electron dissipative end of the electron generation device was placed in the air not to contact metal parts, and then electrons were tried to be dissipated.

However, when mounting, when the coating of the covered electric wire from the power source to the electron dissipative end was damaged, or when the electron dissipative end came into direct contact with the vehicle body due to vibration or the like during driving, even if a protection circuit was provided, the electronic circuit forming the electron dissipating device was sometimes damaged. As a result of this trial, in the case that the in-vehicle battery and the electronic components of the electron generation circuit were short-circuited, it has been found that an undesired overcurrent that exceeds the protection capacity of the protection circuit may flow to the primary-side circuit through one end of the said secondary-side circuit and the electronic circuit may be damaged.

Therefore, the inventor of the present application earnestly studied an electron generation means, in which the secondary-side AC power boosted to high voltage did not need to be returned to the low-voltage primary side as an electronic circuit that generates electrons in a stable state without easily damaging the circuit, and arrived at the present invention.

CITATION LIST

Patent Document

Patent Document 1: Japanese Unexamined Patent Application No. 2005-90338
Patent Document 2: Japanese Unexamined Patent Application No. 2008-38618
Patent Document 3: International Unexamined Patent Application No. 2015-064195
Patent Document 4: Japanese Unexamined Patent Application No. 2009-247200

Non-Patent Document

Non-Patent Document 1: Toyama University Academic Information Repository "Studies on Static Electrification of Non-conductive Liquid (second report) Effect of Non-conductive Liquid on Receiver Tank (page 25 to 27)" by Tottori, Kotaro https://toyama.repo.nii.ac.jp/?action=repository_uri&item_id=3773&file_id=18&file_no=1
Non-Patent Document 2: Technical Data of Japan Petroleum Energy Center, General Incorporated Foundation http://www.pecj.or.jp/japanese/safer/knowledge/doc/no-75.doc

DISCLOSURE OF INVENTION

Problem to be Solved by the Invention

The object of the present invention is to provide an electron generation means that can generate electrons in a stable state even with small power consumption. More in detail, the object is to provide a combustion promoting means, which generates electrons in a stable state with a circuit not easily damaged and promotes combustion by instantaneously gasifying fine particles of fuel injected into an internal combustion engine.

Furthermore, the object is also to provide a moving body with the said electron generation means. Specifically, the object is to provide the moving body that reduces static electricity generated by friction between the moving body and air during movement. Further, a sterilizing/deodorizing means, which sterilizes and deodorizes bacteria that causes foul odor by the liquid charged with electrons generated by the said electron generation means, is to be provided.

Means for Solving Problem

The first invention of the present invention is An electron generation means provided with a rectifier circuit and a booster circuit, in which AC power from a power source is boosted by the said booster circuit for generating electrons from only the one terminal on the secondary side of the said booster circuit, which is characterized as follows: so that current flows in only one direction to the primary side of the said booster circuit, the said rectifier circuit is arranged on the said primary side, and the other terminal on the said secondary side is open; in the state where the first terminal of the said rectifier circuit has a positive potential according to the plus/minus inversion cycle of the AC power, the current to the said booster circuit is blocked by blocking the current from the said first terminal to the said second terminal of the said rectifier circuit; only in the state where the said first terminal has a negative potential, the current flows from the said second terminal to the said first terminal, the current flows toward the primary side of the said booster circuit only in one direction, and the current is generated by mutual induction on the said secondary side; and only in the state where the said first terminal has a negative potential, since the said other terminal is open, the current does not return from the said secondary side to the said primary side, and only electrons are generated from the said one terminal.

Here, the power supply is not limited to a commercial AC power supply but can be a DC power supply. For example, a DC power source such as an in-vehicle battery may be converted into an AC power source by an inverter to be supplied to the electron generation means. The rectifier circuit can be made by providing a known diode or the like between the power supply and the booster circuit so that the current flows only in one direction of the alternating current. In the state where the first terminal of the rectifier circuit has a positive potential, the current in the direction from the first terminal to the second terminal is blocked, so that the current does not flow to the primary-side coil of the booster circuit, and thus no current flows in the secondary-side coil of the booster circuit either. In this cycle, no electrons are generated on the secondary side of the booster circuit.

In the state where the first terminal of the rectifier circuit has negative potential, the current flows in the direction from the second terminal to the first terminal and flows into the primary-side coil of the booster circuit, and thus the current is generated in the secondary-side coil by mutual induction by the two coils. In this cycle, electrons are generated from the one terminal on the secondary side of the booster circuit. Even if the rectifier circuit is inverted and the direction of the current to be blocked is inverted, there is no change that only electrons are generated from the one terminal.

With this, even if the other terminal on the secondary side of the booster circuit is not connected to the primary-side terminal of the booster circuit, only in the state where the first terminal of the rectifier circuit has negative potential, electrons can be generated from the one terminal on the secondary side of the booster circuit. That is, since the high voltage of the secondary side is not returned to the primary side operated at low voltage without connection between the secondary side and the primary side of the booster circuit, each electronic circuit forming the electron generation means is hard to be damaged, and electrons are generated in a stable state.

When specifically explained taking a vehicle as an example, even if the one terminal and metal parts inside the engine compartment contacted temporarily with the vibration caused by driving, the in-vehicle battery, the electronic components of the electron generation circuit, and the metal parts are not in the state of short-circuit, and an unintended overcurrent does not flow in the primary-side circuit.

The booster circuit may be any known booster circuit as long as it can boost the AC power input to the primary side to the desired voltage value and output from the secondary side. The desired voltage value may be determined according to the device to which the electron generation means is applied and is not limited. For example, it is advisable to boost until the voltage, in which electrons can be easily generated while spark discharge does not occur, specifically in the range of 2000V to 5000V.

It is preferable that the booster circuit is operated at high voltage and low current so that the power consumption of the electron generation device is suppressed to the small power consumption of several W. If the secondary side of the booster circuit is boosted to high voltage and electrons are generated at low current, only electrons can be efficiently dissipated with small power consumption.

According to the first invention of the present invention, since the secondary side and the primary side of the booster circuit are not connected, even if an overcurrent occurs due to a short circuit between nearby things and the one terminal, the current is not returned from the secondary side to the primary side of the booster circuit, thus each of the electronic circuits forming the electron generation means is less likely to be damaged, and an advantageous effect not obtainable in the past is achieved that only electrons are generated in a stable state.

The second invention of the present invention is the electron generation means of the first invention and characterized as follows: the said one terminal is provided with an electron transferring means extending linearly; the said electron transferring means has a bundle of fiber conductors at least at a tip portion thereof and dissipates electrons from every single fiber forming the said bundle.

The electron transferring means may be a bundle of fiber conductors as a whole, or only the tip portion is a bundle of fiber conductors, and a base portion connected to the said tip portion may be, for example, a single metal wire. The bundle of fiber conductors refers to a bunch of elongated conductors of fiber wires. The fiber conductor material is not limited, can be a twisted wire formed by twisting a thin metal wire, carbon fiber, or a plated fiber thread in which a metal plating layer is formed around a non-conductive fiber.

Electrons have a characteristic to be dissipated more likely from conductors with a smaller diameter than conductors with a larger diameter. The bundle of carbon fibers has high conductivity, and every single fiber has a diameter smaller than that of a twisted metal wire, and thus it is preferable because it is easier to dissipate electrons. Even at places separated from the main body of the electron generation means, since the electron transferring means with linearly extending shape is provided on the one terminal, electrons can be generated at any desired place.

According to the second invention of the present invention, since the electron transferring means has the bundle of fiber conductors at the tip portion, it is possible to dissipate electrons efficiently with lower power consumption. Furthermore, when applied to a vehicle or the like with an internal combustion engine, electrons can be supplied in the state where the electronic circuit forming the electron generation means is separated from the internal combustion engine of high temperature.

The third invention of the present invention is the electron generation means of the first or the second invention and characterized that the voltage value on the said secondary side is 2000 V or more and 5000 V or less as well as the current value on the said secondary side is 0.2 mA or more and 1 mA or less. Since the voltage value on the secondary side is 2000 V or more and 5000 V or less, it is easy to generate electrons and difficult to produce spark discharge.

The fourth invention of the present invention is a combustion promoting means for promoting combustion of fuel particles sprayed in a fuel combustion space of an internal combustion engine and characterized as follows: the electron generation means according to the first to third inventions is provided; the said one terminal dissipates the said electrons so as not to come into contact with metal parts electrically connected to the internal combustion engine and charges the surrounding metal parts forming the said fuel combustion space with negative electric charge; the said surrounding metal parts attract the said fuel particles by electrostatic attraction and promote vaporization.

When a direct-current in-vehicle battery for starting the internal combustion engine is used as a power source, the direct current may be converted into alternating current by an inverter or the like, and then the alternating current power may be supplied to the electron generation device. The internal combustion engine is not limited to a gasoline engine or a diesel engine mounted on a vehicle, a ship, or the like but may be a thermal power generator. Since the one terminal dissipates the said electrons so as not to contact metal parts that are electrically connected to the internal combustion engine, the circuit forming the electron generation device is less likely to be damaged. Even in the case where electrons are generated to the internal combustion engine at a location exposed to the harsh environment of cold and warm temperatures, the electrons are generated in a stable state.

Fuel particles sprayed into the fuel combustion space come into contact with the metal parts forming the fuel combustion space, such as pistons, a cylinder block, or the like, which are heated into high temperature due to the combustion, are instantly vaporized to finer particles in the form of gas, and thus becomes easily burned. Since the fuel becomes easily burned, a larger amount of kinetic energy can be obtained even with the same fuel amount. According to the fourth invention of the present invention, there is an advantageous effect not provided in the conventional technology that the combustion of fuel is promoted, and the generation of greenhouse gases is suppressed being accompanied by fuel reduction.

The fifth invention of the present invention is the combustion promoting means according to the fourth invention and characterized as follows: the said electron generation means includes a dissipation delaying means; the said dissipation delaying means delays the generation of electrons by generating the said electrons after the metal parts around the said fuel combustion space becomes high temperature exceeding 500° C.

The dissipation delaying means may generate electrons after the metal parts around the fuel combustion space reach a high temperature, and the configuration is not limited. For example, employing a temperature sensor, a timer, or the like, the electron generation device may start at the timing when the temperature of the fuel combustion space exceeds 500° C. after the internal combustion engine is started. Since fuel particles are attracted to the surrounding metal parts forming the fuel combustion space by the electrons after the temperature of the fuel combustion space becomes high, before the temperature of the fuel combustion space becomes high, the fuel particles are not attracted to the surrounding metal parts forming the fuel combustion space. With this, it becomes possible to dissipate electrons and promote combustion only during the period when the fuel is easily vaporized.

The sixth invention of the present invention is the combustion promoting means of the fifth invention and characterized as follows: the said dissipation delaying means includes a temperature detecting means, and the said temperature detecting means detects the temperature of the metal parts around the said fuel combustion space. The temperature detecting means may be a known thermocouple but is not limited.

The temperature detecting means detects that the fuel combustion space has reached a high temperature. With this, even if the outside temperature and the temperature of the internal combustion engine differ depending on the season, region, altitude, or the like, electrons are generated after the fuel combustion space becomes sufficiently high temperature, fuel particles come into contact more preferably to the surrounding metal parts forming the fuel combustion space, and thus the fuel can be gasified to finer particles.

The seventh invention of the present invention is characterized as follows: the combustion promoting means according to the fourth to the sixth invention is mounted on a vehicle; the tip portion of the said one terminal is exposed as well as the base portion connected to the tip portion is provided with the insulation-coated conductive wire; the said insulation-coated conductive wire is mounted on the radiator pipe in the engine room of the said vehicle, and the said tip portion is arranged in the said engine room.

Since the radiator pipe is adjacent to the fuel combustion space, if the conductive wire is attached to around the radiator pipe in a winding manner, the position of the tip portion is less likely to be displaced due to vibration or the like. Further, even if the insulating coating of the conductive wire deteriorates under the high-temperature environment since the radiator pipe is a non-metal part, it does not occur that short-circuiting the conductive wire and the metal parts in the engine room causes high voltage between the metal parts and the first terminal.

With this, even with the electron generation means spending low power consumption, it is easy to charge the metal portion around the fuel combustion space with the electric charge necessary for attracting fuel particles. It is only necessary to arrange the tip of the conductive wire in the engine room, and the electron generation device can be easily applied even to a used car without modification of the internal combustion engine such as the fuel pipe.

The eighth invention of the present invention is a moving body charged with positive static electricity to the moving body itself by the movement accompanied by air resistance and characterized as follows: the electron generation means according to the first to the third inventions is included; the said electron generation means neutralizes the said positive charges by the dissipated electrons, and functions as a static electricity removing means to remove the static electricity of positive charges of the said moving body itself.

The moving body is not limited to an automobile with an internal combustion engine and may be an electric automobile without an internal combustion engine, a fuel cell automobile, a land moving body such as a high-speed railway driven by electricity, or a flying body such as an airplane, a rocket, and not limited. When the moving body moves and air flows along the surface of the moving body itself, the moving body's surface becomes positively charged. When the moving body charged with positive charges moves, the phenomenon of airflow separation from the surface of the moving body itself occurs due to an electrostatic repulsive force between the positive charge of the airflow around the moving body and the positive charge on the surface of the moving body, and the air resistance of the moving body increases. According to the eighth invention, by neutralizing the positive charge of the moving body itself, it becomes possible to suppress an increase in the air resistance of the moving body itself and reduce the power required for the movement.

The sterilization/deodorization means according to the ninth invention of the present invention is the sterilization/deodorization means for dissipating electrons into a stored liquid in which anaerobic bacteria inhabit to sterilize the said anaerobic bacteria as well as deodorize a foul odor, and characterized as follows: the electron generation means according to the first to the third inventions, a ground wire, and an air supply means are included; the said ground wire electrically grounds the said liquid and the ground as well as while the said air supply means supplies foamed air into the said liquid, the said one terminal is immersed in the said liquid and dissipates electrons; the liquid with electrons supplied is stirred by the said air, sterilizes the said anaerobic bacteria, and deodorizes the foul odor.

The liquid to which electrons are dissipated is not limited to polluted water and may be water which people and livestock drink, or water stored in an aquarium of aquatic organisms. Since anaerobic bacteria are considered the cause of the foul odor, as a result of sterilization of the aerobic bacteria, the foul odor is also deodorized. Anaerobic bacteria are weak to electricity and can be sterilized by flowing electrons through the water.

The ground wire may be a covered electric wire with the end exposed. The ground wire electrically grounds the liquid and the ground, and electrons can be continuously dissipated in an environment of constant voltage and current value. The air supply means may be a foaming means for generating bubbles in the water. Since anaerobic bacteria are less likely to reproduce in an environment easily exposed to the air, anaerobic bacteria contained in polluted water can be more effectively sterilized. Further, since the air supply stirs the liquid, the anaerobic bacteria concentration can be reduced without being biased.

According to the ninth invention of the present invention, it is possible to sterilize and deodorize anaerobic bacteria, which cause a foul odor, without using a drug. With this, not only the purification of polluted water but also the advantageous effect is achieved that it is safe for humans and livestock and that a high sterilization/deodorization effect is obtained.

The sterilization/deodorization means of the tenth invention of the present invention is a sterilization/deodorization means for sterilizing anaerobic bacteria as well as deodorizing a foul odor and characterized as follows: the electron generation means according to the first to the third inventions, a tank for storing liquid, a spraying means for the said liquid, a ground wire, and an air supply means are included; the said ground wire electrically grounds the said liquid and the ground as well as while the said air supply means supplies foamed air into the said liquid, the said one terminal is immersed in the said liquid and dissipates electrons and charges the liquid; the said spraying means sprays the charged said liquid to sterilize and deodorize.

The spraying means for the liquid may be a known sprinkler, a sprayer used for spraying pesticides, or a high-pressure washing machine for spraying liquid at high pressure and is not limited. The spraying means and the tank for storing liquid may be integrated or may be separated. The liquid to be sprayed is not limited to water and may be the liquid obtained by diluting an enzyme agent/deodorant in water. Since the water itself storing electrons has a sterilizing and deodorizing effect, in a cleaning work of contaminated floors, even if the enzyme agent, which is diluted 100 times with water when used regularly, is diluted 10,000 times with water, the deodorizing effect equal to or higher than that of the conventional one was obtained.

According to the tenth invention of the present invention, by providing the spraying means, the sterilizing/deodorizing effect can be easily obtained even on a wide contaminated floor or the like. Further, combining an enzyme agent/deodorant agent, which has been conventionally used for sterilization/deodorization, with electrons-storing water, an advantageous effect is achieved that the used amount of enzyme agent or deodorant agent can be significantly reduced.

Effect of the Invention

According to the first invention of the present invention, since the secondary side and the primary side of the booster circuit are not connected, even if an overcurrent occurs due to a short circuit between nearby things and the one terminal, the current is not returned from the secondary side to the primary side of the booster circuit, thus each of the electronic circuits forming the electron generation means is less likely to be damaged, and an advantageous effect not obtainable in the past is achieved that only electrons are generated in a stable state.

According to the second invention of the present invention, since the electron transferring means has the bundle of fiber conductors at the tip portion, it is possible to dissipate electrons efficiently with lower power consumption. Furthermore, when applied to a vehicle or the like with an internal combustion engine, electrons can be supplied in the state where the electronic circuit forming the electron generation means is separated from the internal combustion engine of high temperature.

According to the third invention of the present invention, since the voltage value on the secondary side is 2000 V or more and 5000 V or less, it is easy to generate electrons and difficult to produce spark discharge.

According to the fourth invention of the present invention, there is an advantageous effect not provided in the conventional technology that the combustion of fuel is promoted, and the generation of greenhouse gases is suppressed being accompanied by fuel reduction.

According to the fifth invention of the present invention, it becomes possible to dissipate electrons and promote combustion only during the period when the fuel is easily vaporized.

According to the sixth invention of the present invention, even if the outside temperature and the temperature of the internal combustion engine differ depending on the season, region, altitude, or the like, electrons are generated after the fuel combustion space becomes sufficiently high temperature, fuel particles come into contact more preferably to the surrounding metal parts forming the fuel combustion space, and thus the fuel can be gasified to finer particles.

According to the seventh invention of the present invention, even with the electron generation means spending low power consumption, it is easy to charge the metal portion around the fuel combustion space with the electric charge necessary for attracting fuel particles. It is only necessary to arrange the tip of the conductive wire in the engine room, and the electron generation device can be easily applied even to a used car without modification of the internal combustion engine such as the fuel pipe.

According to the eighth invention of the present invention, by neutralizing the positive charge of the moving body itself, it becomes possible to suppress an increase in the air resistance of the moving body itself and reduce the power required for the movement.

According to the ninth invention of the present invention, not only the purification of polluted water but also the advantageous effect is achieved that it is safe for humans and livestock and that a high sterilization/deodorization effect is obtained.

According to the tenth invention of the present invention, by providing the spraying means, the sterilizing/deodorizing effect can be easily obtained even on a wide contaminated floor or the like. Further, an advantageous effect is achieved that the used amount of enzyme agent or deodorant agent can be significantly reduced.

BEST MODE(S) FOR CARRYING OUT THE INVENTION

In the electron generating means for generating electrons, before AC power from the power supply is passed to the booster circuit, the rectifier circuit rectifies the current beforehand to flow only in the state where the first terminal of the rectifier circuit has negative potential, and electrons are to be generated only from the one terminal on the secondary side in the booster circuit. In the combustion promoting means, the said electrons are supplied to the internal combustion engine, and fuel particles are attracted to the surrounding metal parts forming the fuel combustion space by electrostatic attraction to promote vaporization.

In the moving body, the phenomenon caused by the movement of the moving body charged with a positive charge that airflow is separated from the surface of the moving body itself due to electrostatic repulsive force between the airflow around the moving body and the surface of the moving body is suppressed by neutralizing the positive charge of the moving body itself, and the increase of air resistance is suppressed. Further, in the sterilization/deodorization means, the liquid is charged by the said electrons, and the liquid charged with electrons sterilizes the anaerobic bacteria and deodorizes the foul odor.

Example 1

Figure 1A:
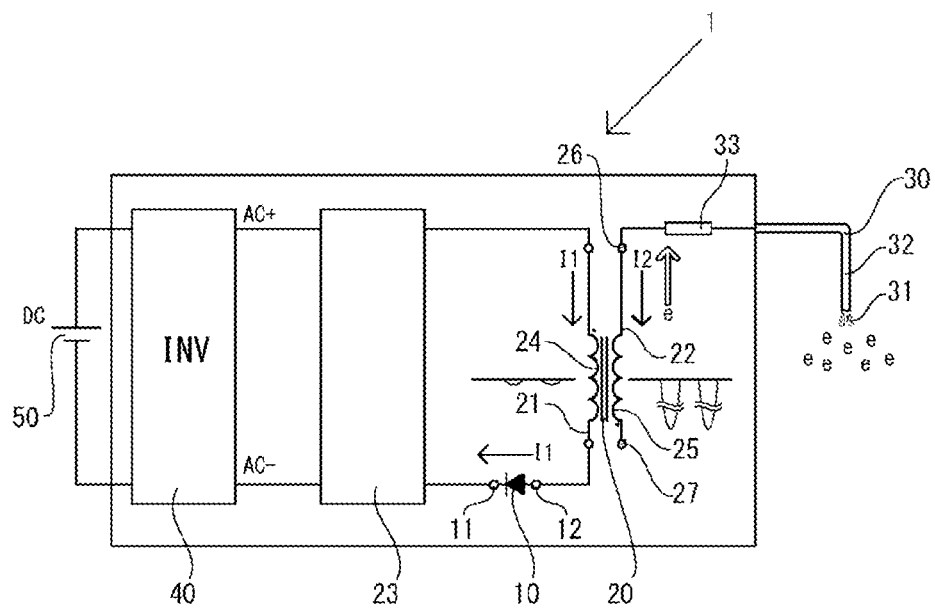
FIGS. 1(A) and 1(B) are explanatory drawings of the electron generation means (Example 1).
Figure 1B:
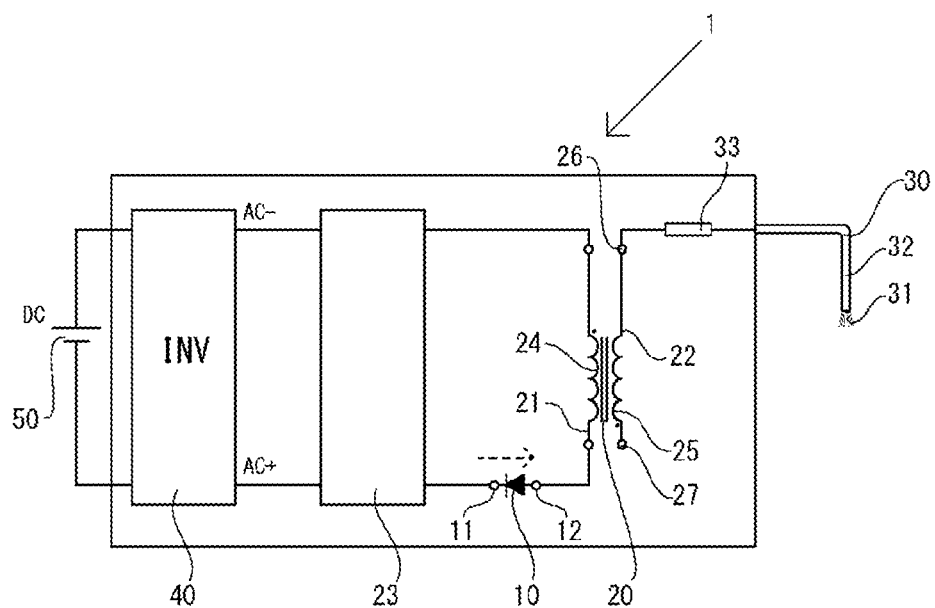

In example 1, the configuration and operation of the electron generation means 1 are described with reference to FIGS. 1(A) and 1(B). FIG. 1(A) shows the state where electrons are generated from the one terminal on the secondary side of the booster circuit, and FIG. 1(B) shows the state where the rectifier circuit blocks the current. In FIG. 1(A), an arrow indicates the direction of the current, and a white arrow indicates the electron flow direction. The voltage waveform applied to each coil forming the booster circuit is shown next to each coil.

The electron generation means 1 includes the rectifier circuit 10, the booster circuit 20, a linearly extending electron transferring means 30, and an inverter 40 for converting DC power into AC power. The AC power supplied to the electron generation means 1 is obtained by converting the DC power from the in-vehicle battery 50 of DC 12V or 24V into the AC power of 12V or 24V by the known inverter 40.

In the electron generation means 1 of the example 1, the rating setting circuit is designed so that the rated capacity of the primary-side circuit 21 of the booster circuit 20 is 1 W, the voltage value is 12 V, and the current value is about 0.083 A; the turn ratio of the booster circuit is set so that the voltage value is 5000 V and the current value is about 0.2 mA in the secondary-side circuit 22. The rating setting circuit 23 may be appropriately set according to the amount of electrons generated by the electron generation means.

The rectifier circuit 10 is a known diode and is arranged in the primary-side circuit 21 of the booster circuit. Specifically, in the rectifier circuit 10, the first terminal 11 side, forming the cathode terminal of the diode, is connected to the power supply side, and the second terminal 12 side, forming the anode terminal, is connected to the primary coil 24 side, forming the booster circuit. With this, AC power from the power supply passes through the rectifier circuit 10 in advance and then flows into the booster circuit 20.

The booster circuit 20 may be any known booster circuit and boosts the voltage value input to the primary-side circuit 21 and outputs from the secondary-side circuit 22. The booster circuit 20 has a winding number ratio of the primary coil 24 and the secondary coil 25 set so that a voltage value of 5000 V can be output from the secondary side according to the voltage value of the primary side. In the secondary-side circuit 22 of the booster circuit, the electron transferring means 30 attaches to the one terminal 26, and the other terminal 27 is in the state of being connected to none.

The electron transferring means 30 has a bundle of carbon fibers at the tip portion 31, and the base portion 32 connected to the said tip portion 31 is an insulation-coated twisted metal wire. Electrons are dissipated from every single fiber forming the bundle of carbon fibers. A current limiting resistor 33 is provided between the one terminal 26 to generate electrons, and the electron transferring means 30, and the current value transferred to the electron transferring means is limited to a low value of about 0.2 mA.

Next, the operation of the electron generation means 1 will be described by comparing FIG. 1(A) and FIG. 1(B). The direction of the current applied to the rectifier circuit is periodically inverted according to the positive/negative inversion period of AC power from the power supply. According to the electron generation means 1 of the present invention, in the state where the first terminal 11 of the rectifier circuit has positive potential according to the positive/negative inversion cycle of the said AC power (FIG. 1(B)), the current flowing from the first terminal 11 to the second terminal 12 is blocked. On the other hand, in the state where the first terminal 11 of the rectifier circuit has negative potential (FIG. 1(A)), the current (the arrow I1 in the figure) flowing to the second terminal 12 is not blocked, and the current flows from the second terminal 12 to the first terminal 11 in the opposite direction.

Then, in the state where the first terminal 11 of the rectifier circuit has negative potential, the secondary-side circuit 22 of the booster circuit also has a current flowing from the one terminal 26 to the other terminal 27 (FIG. 1(A), refer to the arrow I2). Since the direction of electron flow is opposite to the direction of current flow, in the secondary-side circuit 22 of the booster circuit, electrons are supplied from the one terminal 26 toward the electron transferring means 30 (FIG. 1(A), refer to the white arrow in the figure). Therefore, without returning the current from the secondary-side circuit 22 of the booster circuit to the primary-side circuit 21, electric power is supplied to the booster circuit only for a period of ½ cycle, and electrons are generated only during the period when the secondary-side circuit 22 of the booster circuit is supplied with the electric power.

Example 2

Figure 2:
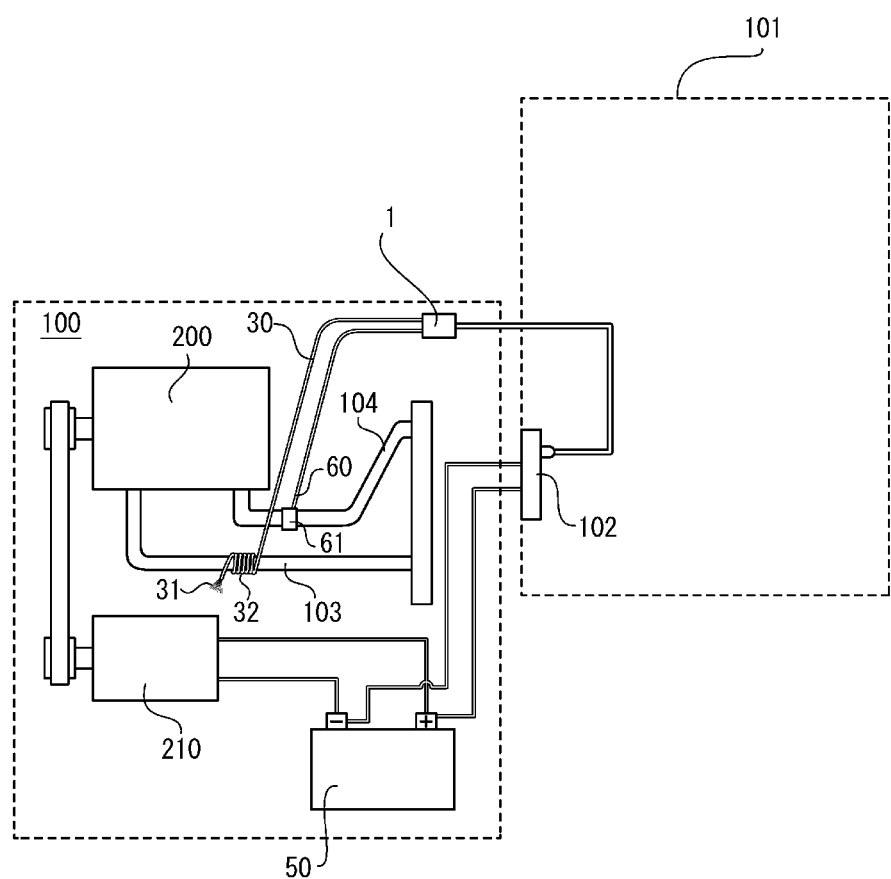
FIG. 2 is an explanatory drawing of the automobile with the combustion promoting means (Example 2).
Figure 3A:
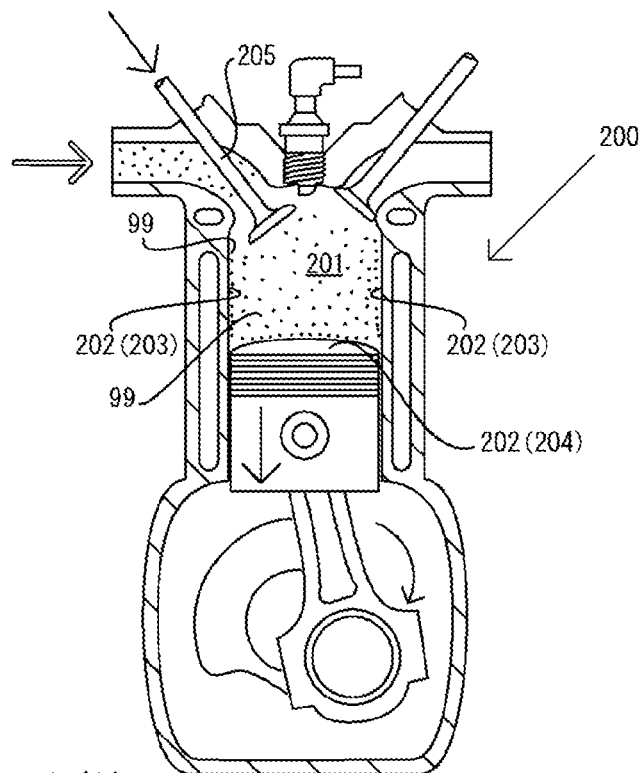
FIGS. 3(A) and 3(B) are explanatory drawings of the combustion promoting means (Example 2).
Figure 3B:
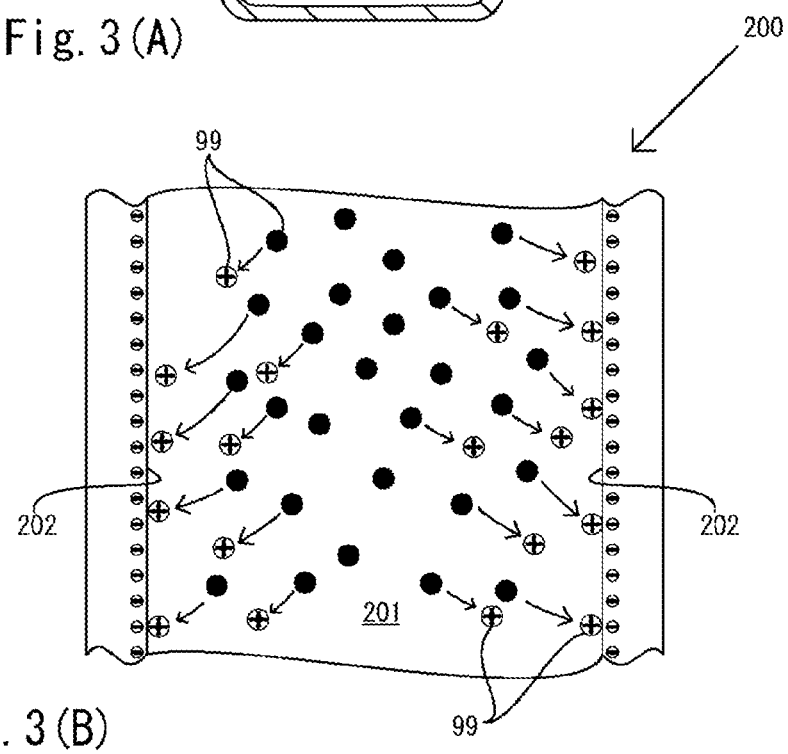
Figure 6:
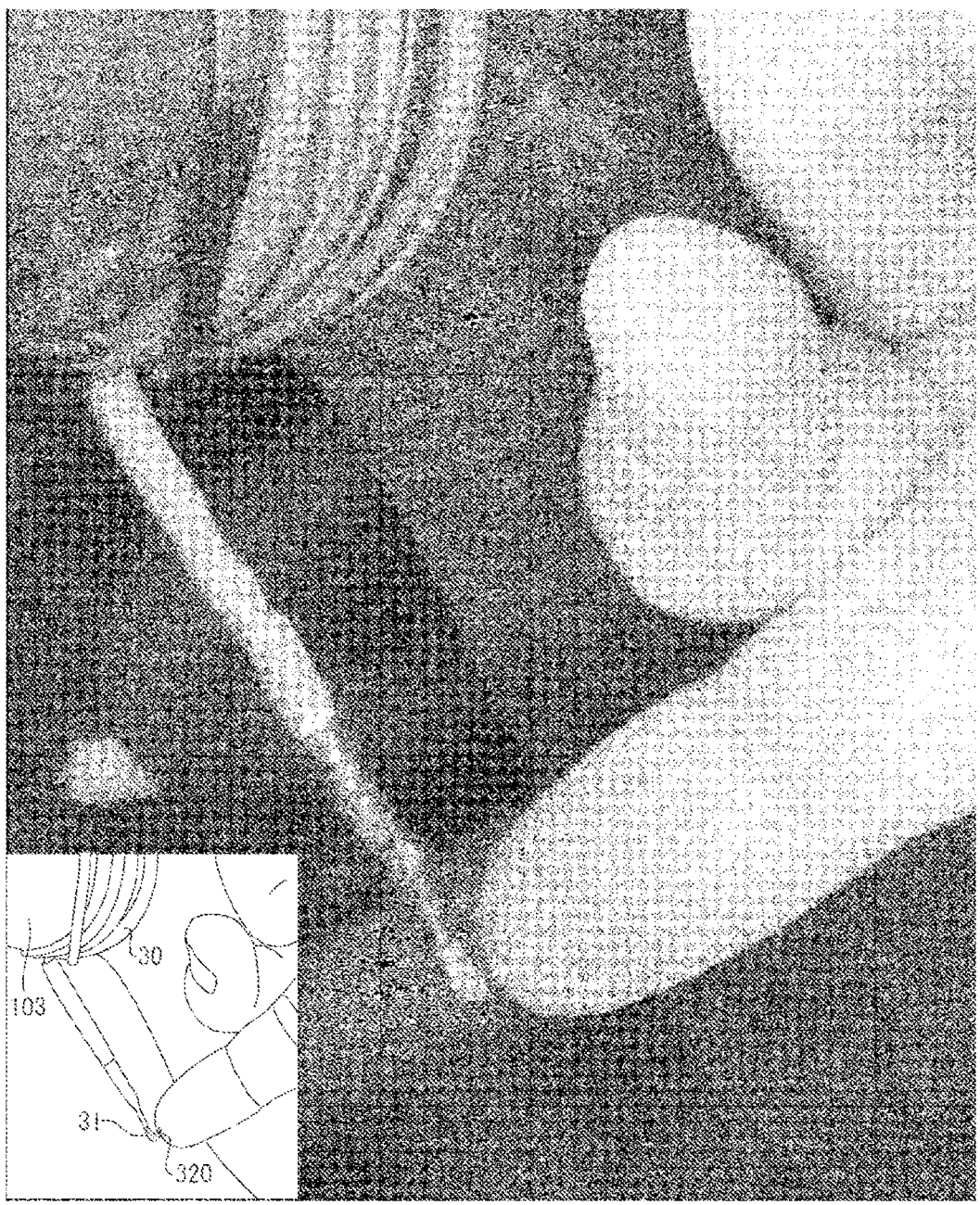
FIG. 6 is a photo and an explanatory drawing to show the state of electrons being generated (Example 2).

In example 2, the combustion promoting means, and the static electricity removing means for removing the positive static electricity charged in the vehicle are described with reference to FIGS. 2 to 4(B) and 6. FIG. 2 shows the state in which the used vehicle is equipped with the electron generation means 1, which forms the combustion promoting means and the static electricity removing means. FIGS. 3(A) and 3(B) show a schematic diagram by partial cross-sections of the internal combustion engine. FIG. 3(A) shows the state where the air-fuel mixture is injected into the fuel combustion space of the internal combustion engine, and FIG. 3(B) shows an enlarged diagram of the said fuel combustion space. FIG. 6 shows a photograph showing the state where electrons are generated from the electron generation means, and an explanatory diagram at the lower-left corner, which explains the photograph.

In FIG. 3(A), each component's operation direction is indicated by an arrow, and a white arrow indicates the introduction direction of the mixture of fuel particles and the air. In FIG. 3(B), electrons are shown by minus signs enclosed in circles, and fuel particles are shown by plus signs enclosed in circles. Further, the positions before the fuel particles are attracted to the electrons are indicated by black circles, and arrows indicate the attracted movements.

Figure 4A:
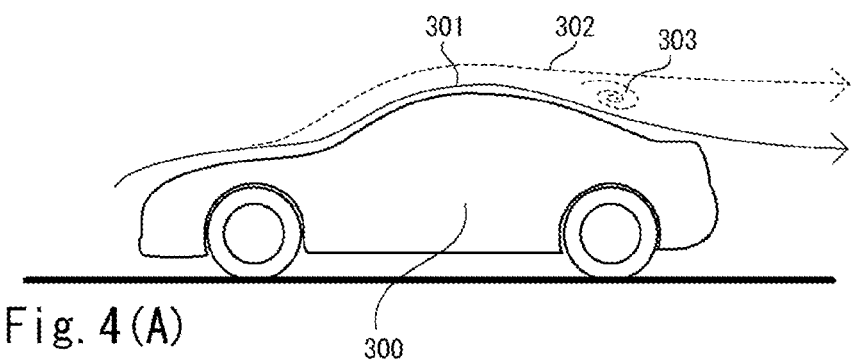
FIGS. 4(A) and 4(B) are explanatory drawings of moving bodies with the static electricity removing means (Example 2).
Figure 4B:
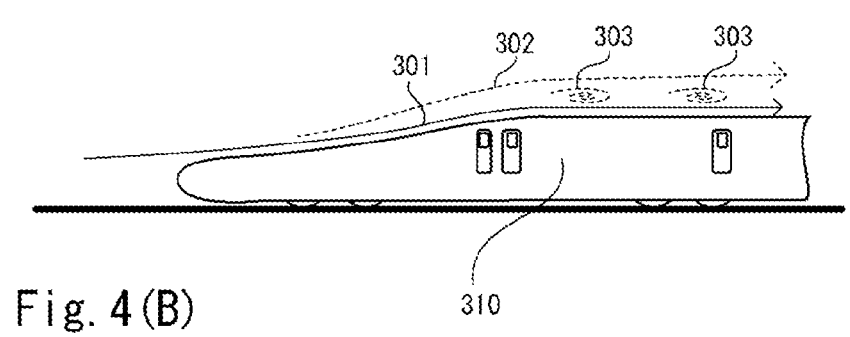

FIGS. 4(A) and 4(B) show a moving body in which the electron generation means 1 functions as the static electricity removing means. FIG. 4(A) is a schematic diagram of the surrounding airflow which occurs while the automobile is running. FIG. 4(B) shows a schematic diagram of the airflow in the case of a high-speed railway. In each drawing of FIGS. 4(A) and 4(B), the state where air flows along the moving body is shown by a solid line, and a broken line indicates the state where air flows apart from the moving body itself. Besides, vortexes due to the separated airflow are shown by broken lines.

First, the method of mounting the electron generation means 1 on a used car is described with reference to FIG. 2. Although the mounting position of the main body of the electron generating means 1 is not limited, the main body was mounted in the engine room 100 in the running test described later. The power source of the electron generation means is DC power obtained from the cigar socket 102 arranged in the driver's seat 101, and this DC power is converted into AC power by the inverter incorporated in the electron generation means 1.

The main body of the electron generation means is provided with the electron transferring means 30 shown in example 1, and the dissipation delaying means 60 for delaying the start of the electron generation means 1. The used vehicle equipped with the electron generation means was subjected to running tests on both a cargo carrier driven by a diesel engine and a passenger car driven by a gasoline engine, as described later.

The insulation-coated base portion 32 of the electron transferring means 30 is mounted by winding a plurality of times around the outward pipe 103 of the radiator pipe, which circulates cooling water in the internal combustion engine. The bundle of carbon fibers provided at the tip portion 31 of the electron transferring means dissipates electrons so as not to come into contact with the metal parts inside the engine room 100 or of the internal combustion engine 200. The bundle of carbon fibers forming the said tip portion 31 charges in the vicinity of the generator 210 the surrounding metal parts which form the fuel combustion space of the internal combustion engine 200 with a negative charge.

The dissipation delaying means 60 is equipped with a temperature sensor 61 which forms a temperature detecting means. The temperature sensor 61 is attached to the return pipe 104 of the radiator pipe and detects from the temperature of the cooling water circulated in the radiator pipe that the internal temperature of the metal parts forming the internal combustion engine 200 exceeds the predetermined temperature. For example, it is enough to detect from the cooling water temperature that the said internal temperature had reached 500° C.

Here, the state where the fuel particles are vaporized in a gaseous state is described with reference to each diagram of FIGS. 3(A) and 3(B) in a four-stroke engine as an example. The surrounding metal parts 202 that form the fuel combustion space 201 of the internal combustion engine are a cylindrical cylinder 203, a piston 204 which slides along the cylinder's inner peripheral surface, and the like. In the state where the said surrounding metal parts 202 are charged with a negative charge by electrons, the intake valve 205 opens, and the piston 204 slides downward by the crank movement so that the mixed air of atomized fuel particles 99 and air is sprayed into the fuel combustion space 201 (refer to FIG. 3(A)).

As described earlier, the fuel particles 99 are positively charged by friction with the pipe wall and the like during being supplied to the fuel combustion space through the fuel pipe from the fuel tank. Then, the atomized fuel particles 99 sprayed into the fuel combustion space have a positive charge and are attracted by electrostatic attraction to the surrounding metal parts 202 charged with a negative charge (refer to the arrow in FIG. 3(B).)

The fuel particles attracted to the surrounding metal parts 202 of the fuel combustion space become instantly into finer particles in contact with the surrounding metal parts 202, the temperature of which became high due to combustion, and are gasified and become the state to burn quickly. Since the fuel becomes the state to burn quickly, even with the same amount of fuel, a more considerable amount of kinetic energy can be extracted without waste.

Further, the air 301 flowing along the moving body 300 (as an example, an automobile vehicle is shown in FIG. 4(A)) during continuous running accompanied by air resistance takes out negative charge from the moving body, and positive-charged static electricity remains being charged on the moving body. When the moving body 300 is charged with positive-charged static electricity, the air 302 charged with a positive charge is repelled by electrostatic repulsive force, and the airflow flowing along the moving body separates from the moving body itself, then the separation thereby generates vortexes 303 (refer to the broken line arrow in FIG. 4(A)). The air resistance applied to the moving body 300 increases by generating the vortexes 303 compared with the state where the air is flowing along near the moving body (refer to the solid line arrow in FIG. 4(A)).

In the present invention, since electrons are being dissipated in the engine room 100 of the automobile vehicle (refer to FIG. 2), the moving body itself is also negatively charged by the said electrons. Therefore, even if negative charge is taken out from the moving body itself by the airflow during running associated with air resistance, it is difficult for the moving body itself to be charged with positive-charged static electricity, and the airflow remains flowing along the moving body 300; thus it is difficult for the air resistance to increase due to running. This is similar even to the case of the high-speed railway 310 (refer to FIG. 4(B)). As described above, with the fact that the fuel combustion is promoted and the increase in the air resistance applied to the vehicle is suppressed, the verification test described later verified that the remarkable improvement effect of the fuel consumption rate was obtained.

Moreover, to verify that electrons are being generated, whether an electrostatic discharge occurs is confirmed by putting hands inside the engine room. FIG. 6 shows the state where the finger came close to the tip portion 31 of the electron transferring means 30, and the spark discharge 320 is forcibly generated. During the process of bringing the finger closer to the said tip portion, irritation caused by the static electricity was felt on the hand. With this, it was confirmed that electrons were generated from the electron generation means, and a negative charge was supplied to the entire inside of the engine room.

(Verification Test 1)

In verification test 1, an electron generation means was mounted on a cargo carrier which had been used for a long-distance transportation for 13 years after the production (the specifications: a diesel engine with a displacement of 12,910 cc as a motor, a maximum load capacity of 12.8 t, and a vehicle weight of 12.08 t), and a long-term running test was conducted. The specifications of the electron generation means are described in example 1, and the mounting method of the electron generation means is as shown in FIG. 2. Since the verification test 1 was conducted for a long time of continuous running, the test was conducted without causing the dissipation delaying means to function.

In verification test 1, a driver who has been driving the said cargo carrier for 13 years conducted the running test on a public road of a speed limit of 60 km/h being used for everyday work during about two months of the test period, from Sep. 25, 2018, to Nov. 20, 2018. The load of the cargo carrier varied day by day but averaged about 70% to 90% of the maximum load capacity.

The comparison data in the case where the electron generation means was not mounted was the data for one month from Aug. 1, 2018, to Aug. 31, 2018, before mounting the electron generation means. The conditions such as the main running route, the running place, the driver, the load, and the like were almost the same. The mileage was measured by the odometer installed in the vehicle, and the fuel consumption was the cumulative amount of fuel refueled during the test period.

The results of the verification test 1 are shown in Table 1 below, comparing the case where the electron generation means was mounted, and the case where the electron generation means was not mounted. The total mileage for two months of the case where the electron generation means was mounted was 21,616 km, and the fuel refueling amount was 5,507 liters. The fuel consumption rate of the case where the electron generation means was mounted was about 3.9 km/liter.

On the other hand, in the case where the electron generation means was not mounted, the total mileage for one month was 12,350 km, and the fuel refueling amount was 3,972 liters. The fuel consumption rate in the case where the electron generation means was not mounted was about 3.1 km/liter. This verification test 1 verified that the fuel consumption rate improved by about 26%.

From the results of this verification test 1, it resulted that a remarkable improvement effect of the fuel consumption rate was obtained in the cargo carrier that runs long-distance continuously. It is recognized that the effect of improving the fuel consumption rate is due to the synergistic effect of promoting the combustion of fuel and reducing air resistance during running.

TABLE 1

|  | with electron generation means | without electron generation means |
| --- | --- | --- |
| Mileage [km] | 21,616 | 12,350 |
| Fuel consumption [l] | 5,507 | 3,972 |
| Fuel consumption rate [km/l] | 3.9 | 3.1 |
| Running period | 2018 Sep. 25- 2018 Nov. 20 | 2018 Aug. 1- 2018 Aug. 31 |

(Verification Test 2)

In verification test 2, using a gasoline engine with a displacement of 1968 cc as the main motor and an eight-passenger minivan type passenger car which is 1.62 tons of the vehicle weight and passed 7 years after production, the situation of attraction of fuel particles by electrostatic attraction to the metal parts inside the fuel combustion space was tested. According to the odometer mounted on the vehicle, the average fuel consumption rate in the past 7 years without the electronic generation means was about 9.4 km/liter. In the past 7 years, short-distance and short-time running of about 3 km each way mainly on public roads in an urban area on each day of weekdays have been the mainstream, and long-distance running of 400 km round trip to the suburbs has been done once every two months.

As the running test with an electron generation device mounted, the fuel consumption rate in the case of running short-distance/short-time round trip of 3 km each way mainly on weekdays and the fuel consumption rate in the case of long-distance/continuous running on public roads were compared. The results of the verification test 2 are shown in Table 2 below.

First, with winter tires installed and riding one adult driver and one infant, the short-distance/short-time running tests on public roads in an urban area in the state where the engine did not reach high temperature were conducted for one month from Nov. 10, 2018, to Dec. 10, 2018. Next, with remaining the winter tires installed and riding two adults, including the driver, the long-distance/continuous running test on public roads in the suburbs in the case where the engine reached high temperature was conducted for one day on Dec. 23, 2018.

In the winter, since the engine does not reach a high temperature in the short-distance/short-time roundtrip running of 3 km each way, 44.5 liters of gasoline were consumed in the running distance of about 291.0 km, and the average fuel consumption rate deteriorated to about 6.54 km/liter. As a result, the fuel consumption rate during the short-distance/short-time running was deteriorated by about 30% compared with the past cumulative data in which the electronic generation device was not mounted. This result demonstrates that, in addition to wearing winter tires, the fuel adhered to the metal parts of the fuel combustion space before becoming high temperature, and thus the sliding resistance of the pistons of the internal combustion engine increased.

On the other hand, in the long-distance/continuous running in which the engine maintains a state of high temperature, 18.5 liters of gasoline are consumed in the running distance of about 236.1 km, and the fuel consumption rate improved to about 12.76 km/liter. Even with the winter tires installed, the fuel consumption rate for the long-distance/continuous running improved by about 35% compared to the cumulative fuel consumption rate in the past when the electronic generation device was not mounted. From the results of the verification test 2, that the fuel burns efficiently in the long-distance/continuous running in which the internal temperature of the engine became high was verified.

The fact that even if the same driver drove the same vehicle in the same period, the result of the fuel consumption rate of the long-distance/long-time running test became the value of 1.95 times that of the short-distance/short-time running, demonstrates as follows: the gasoline was attracted to the negatively charged metal parts of the engine; in the case where the metal parts were not high temperature, the sliding resistance increased and the fuel consumption rate deteriorated; and in the case where the metal parts were high temperature, gasification of the gasoline was promoted, and the fuel consumption rate improved.

TABLE 2

|  | short-dist./ short-time running on urban roads (3 km each way) | long-dist./ continuous running on suburban roads |
| --- | --- | --- |
| Mileage [km] | 291.0 | 236.1 |
| Fuel consumption [l] | 44.5 | 18.5 |
| Fuel consumption rate [km/l] | 6.54 | 12.76 |
| Running period | 2018 Nov. 10- 2018 Dec. 10 | 2018 Dec. 23 |

Example 3

Figure 5A:
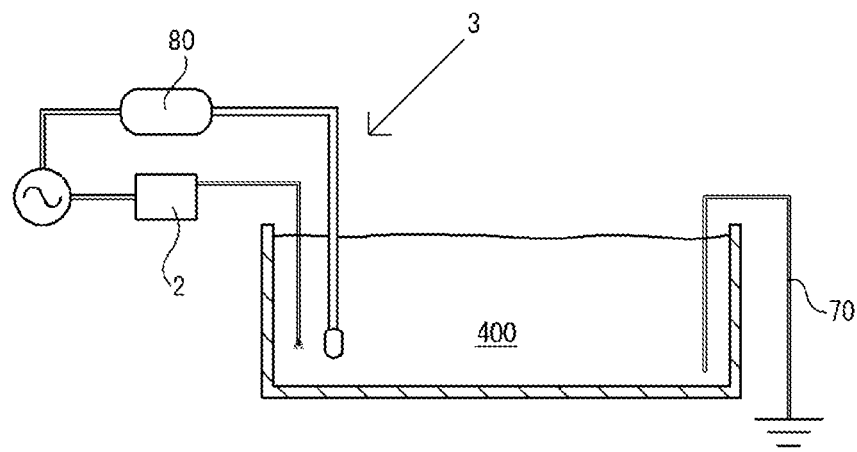
FIGS. 5(A) and 5(B) are explanatory drawings of the sterilization/deodorization means (Example 3).
Figure 5B:
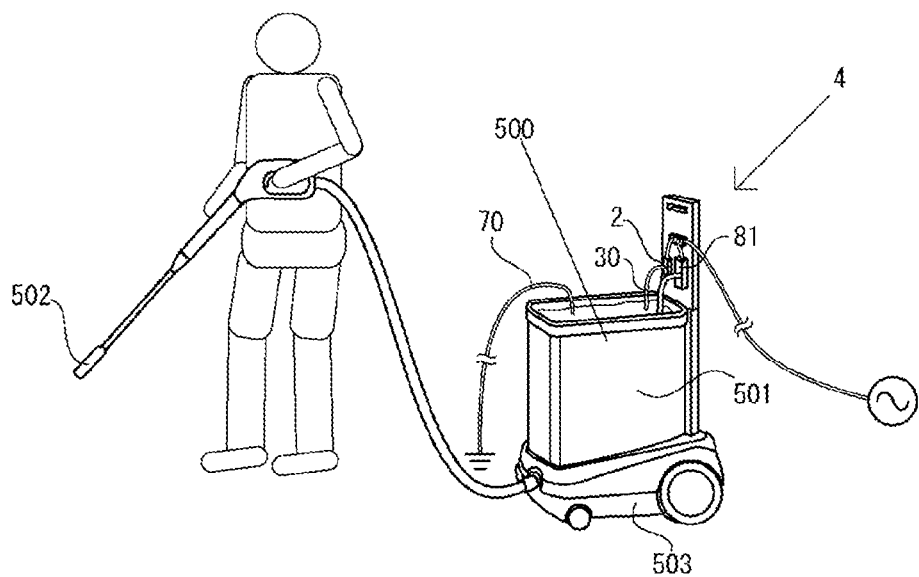

In example 3, the sterilization/deodorization means 3 is described with reference to FIGS. 5(A) and 5(B). FIG. 5(A) shows a sterilization/deodorization means 3 for sterilizing/deodorizing polluted water discharged from a food factory or the like, and FIG. 5(B) shows a sterilization/deodorization means 4 for sterilizing/deodorizing contaminated floor or the like by spraying water charged with electrons with a spray means.

In the sterilization/deodorization means 3, an example of sterilizing *Escherichia coli* contained in polluted water discharged from the food factory as well as deodorizing foul odor caused by *Escherichia coli* is described with reference to FIG. 5(A). The sterilization/deodorization means provides with an electron generation means 2, a ground wire 70 for electrically grounding the polluted water to the ground, and an air supply means for supplying air into the polluted water.

Since the electron generation means 2 uses a commercial AC power supply of AC 100V, compared with the electron generation means described in example 1, the built-in inverter is removed, the winding numbers of the primary coil and the secondary coil which form a booster circuit are different, and the other configurations are the same. The ground wire 70 is a twisted stainless wire that does not rust even immersed in water. The ground wire is inserted into the ground to a depth of about 60 cm and electrically grounded. The air supply means is a foaming means 80 for supplying air bubbles into the liquid. The foaming means are shown for each verification test because the used equipment differs depending on the liquid volume that allows electrons to flow.

(Verification Test 3)

In verification test 3, the test was conducted to sterilize and deodorize the polluted water in the sewage treatment tank 400 drained from a bento factory of a small-scale retail store, which is developing a franchise chain. The volume of polluted water was 1800 tons; the electron generation means 2 of one equipment of 1 W, 100 V, and 10 mA is used, boosted the voltage value of the secondary-side circuit to 5000 V, and continued to dissipate electrons for 72 hours, and the number of *Escherichia coli* was confirmed.

The foaming means 80 is an air supply pump initially installed in the sewage treatment tank 400. The air supply performance per machine is 45 $m^3$/hour, the effective capacity against water per machine is 50 $m^3$, and 40 units are installed being dispersed in the sewage treatment tank 400. The sample of *Escherichia coli* number was measured at Toyo Environmental Laboratory Co., Ltd. The *Escherichia coli* number before the sterilization/deodorization is compared with the *Escherichia coli* number after the sterilization/deodorization, and the results of the verification test 3 are shown in Table 3 below. The measuring method of *Escherichia coli* is based on "Ordinance of Ministry of Health and Welfare/Ministry of Construction No. 1 of 1962" of Japan.

The number of *Escherichia coli* contained in the contaminated water was 3100/$cm^3$ before the sterilization/deodorization. On the other hand, after the sterilization/deodorization in which electrons were continuously dissipated for 72 hours, the number became 130/$cm^3$. The effect of reducing *Escherichia coli* by about 95.8% was obtained with the dissipation of electrons.

TABLE 3

|  | before sterilization/ deodorization | after sterilization/ deodorization |
| --- | --- | --- |
| Number of *Escherichia coli* [pc./$cm^3$] | 3100 | 130 |

The sterilizing/deodorizing means 4 (refer to FIG. 5(B)) is a high-pressure washing machine 500 including the said electron generation means 2, the ground wire 70, the foaming means 81, and the spraying means. The high-pressure washing machine 500 is provided with a water storage tank 501 whose upper side is open, a sprayer 502 for spraying water stored in the water storage tank, and a main body 503 with an internal pump supplying water at high pressure to the sprayer. The electron transferring means 30 extending from the electron generation means 2, the ground wire 70, and the foaming means 81 were immersed in the water storage tank 501, and the water was sprayed by the sprayer 502 while electrons were dissipated in the water.

The water storage tank 501 of the high-pressure washing machine has a capacity of about 20 liters. Water in a water storage tank of 240 tons in which electrons have been dissipated beforehand by the sterilization/deodorization means 3 is transferred to the said water storage tank 501 for the usage. Since the water with electrons charged beforehand is used, it is unnecessary to wait for the cleaning work until electrons are charged. Further, since electrons are also being dissipated in the water storage tank 501 itself of the high-pressure washing machine, the high sterilizing ability is maintained over the entire time of the cleaning work.

A foaming means (not shown) used in the large-capacity water storage tank was an air supply pump for a septic tank with 80 liters/minute air supply capacity. The foaming means used in the water storage tank of the high-pressure washing machine was an air supply pump for aquatic organisms with 0.6 l/min air supply capacity.

(Others)

In the embodiments, the examples in which the electron generation means is applied to the combustion promoting means, the static electricity removing means, and the sterilizing/deodorizing means have been described, but needless to say, the application range of the electron generation means of the present invention is not limited to these.

In example 3, although an example of grounding that the ground wire was buried in the ground was described, in the case where the present invention is used indoors, of course, grounding can be done by connecting the ground wire to a ground terminal provided on the electric wiring. Also, an example was described in which water charged with electrons is transferred to the high-pressure washing machine to be sprayed, but it is also possible that water may be directly drawn up from the large-capacity storage tank and sprayed.

The embodiments disclosed here are illustrative examples in all respects, and it should be considered that the embodiments are not restrictive. The technical scope of the present invention is shown by claims without being restricted to the above explanation, and all modifications are intended to be included in the same meaning and range as the claims.

REFERENCE SIGNS LIST 1, 2 . . . Electron generation means,
3, 4 . . . Sterilization/Deodorization means,
10 . . . Rectifier circuit, 20 . . . Booster circuit,
30 . . . Electron transferring means, 40 . . . Inverter,
50 . . . In-vehicle battery,
11 . . . First terminal, 12 . . . Second terminal,
21 . . . Primary-side circuit, 22 . . . Secondary-side circuit,
23 . . . Rating setting circuit, 24 . . . Primary coil,
25 . . . Secondary coil, 26 . . . One terminal, 27 . . . Other terminal,
31 . . . Tip portion, 32 . . . Base portion,
33 . . . Current limiting resistor,
60 . . . Dissipation delaying means, 61 . . . Temperature sensor,
70 . . . Ground wire, 80, 81 . . . Foaming means,
99 . . . Fuel particles,
100 . . . Engine room, 200 . . . Internal combustion engine,
210 . . . Generator,
101 . . . Driver's seat, 102 . . . Cigar socket,
103 . . . Outward pipe, 104 . . . Return pipe,
201 . . . Fuel combustion space, 202 . . . Surrounding metal part,
203 . . . Cylinder, 204 . . . Piston, 205 . . . Intake valve,
300 . . . Moving body, 301, 302 . . . Air, 303 . . . Vortex,
310 . . . High-speed railway, 320 . . . Spark discharge,
400 . . . Sewage treatment tank,
500 . . . High-pressure washing machine,
501 . . . Water storage tank, 502 . . . Sprayer, 503 . . . Main body

The invention claimed is:

1. An electron generation means provided with a rectifier circuit and a booster circuit, in which AC power from a power source is boosted by the said booster circuit for generating electrons from only one terminal on a secondary side of the said booster circuit, which is characterized as follows:

so that current flows in only one direction to a primary side of the said booster circuit, the said rectifier circuit is arranged on the said primary side, and the other terminal on the said secondary side is open;

in the state where the first terminal of the said rectifier circuit has a positive potential according to the plus/minus inversion cycle of the AC power, a current to the said booster circuit is blocked by blocking the current from the said first terminal to the said second terminal of the said rectifier circuit only in the state where the said first terminal has a negative potential, the current flows from the said second terminal to the said first terminal, the current flows toward the primary side of the said booster circuit only in one direction, and the current is generated by mutual induction on the said secondary side; and only in the state where the said first terminal has a negative potential, since the said other terminal is open, the current does not return from the said secondary side to the said primary side, and only electrons are generated from the said one terminal.

2. The electron generation means according to claim 1, wherein the said one terminal is provided with an electron transferring means extending linearly; and the said electron transferring means has a bundle of fiber conductors at least at a tip portion thereof and dissipates electrons from every single fiber forming the said bundle.

3. The electron generation means according to claim 1, wherein a voltage value on the said secondary side is 2000 V or more and 5000 V or less, and a current value on the said secondary side is 0.2 mA or more and 1 mA or less.

4. The electron generation means according to claim 2, wherein the voltage value on the said secondary side is 2000 V or more and 5000 V or less, and a current value on the said secondary side is 0.2 mA or more and 1 mA or less.

5. A combustion promoting means for promoting combustion of fuel particles sprayed in a fuel combustion space of an internal combustion engine and characterized as follows:

the electron generation means according to any one of claim 1 to claim 4 is included;

the said one terminal dissipates the said electrons so as not to come into contact with metal parts electrically connected to the internal combustion engine and charges surrounding metal parts forming the said fuel combustion space with negative electric charge; and the said surrounding metal parts attract the said fuel particles by electrostatic attraction and promote vaporization.

6. The combustion promoting means according to claim 5, wherein the said electron generation means includes a dissipation delaying means; and the said dissipation delaying means delays the generation of the electrons by generating the said electrons after the metal parts around the said fuel combustion space becomes high temperature exceeding 500° C.

7. The combustion promoting means according to claim 6, wherein the said dissipation delaying means includes a temperature detecting means; and the said temperature detecting means detects the temperature of the metal parts around the said fuel combustion space.

8. The combustion promoting means according to claim 5, wherein the said combustion promoting means is mounted on a vehicle;

the tip portion of the said one terminal is exposed as well as a base portion connected to the tip portion is provided with an insulation-coated conductive wire;

the said insulation-coated conductive wire is mounted on a radiator pipe in an engine room of the said vehicle, and the said tip portion is arranged in the said engine room.

9. The combustion promoting means according to claim 6, wherein the said combustion promoting means is mounted on a vehicle;

the tip portion of the said one terminal is exposed as well as a base portion connected to the tip portion is provided with an insulation-coated conductive wire;

the said insulation-coated conductive wire is mounted on a radiator pipe in an engine room of the said vehicle, and the said tip portion is arranged in the said engine room.

10. The combustion promoting means according to claim 7, wherein the said combustion promoting means is mounted on a vehicle;

the tip portion of the said one terminal is exposed as well as a base portion connected to the tip portion is provided with an insulation-coated conductive wire;

the said insulation-coated conductive wire is mounted on a radiator pipe in an engine room of the said vehicle, and the said tip portion is arranged in the said engine room.

11. A moving body which is charged with positive static electricity to the moving body itself by movement accompanied by air resistance, wherein the electron generation means according to any one of claim 1 to claim 4 is included; and the said electron generation means neutralizes positive charges by the dissipated electrons, and functions as a static electricity removing means to remove the static electricity of the positive charges of the said moving body itself.

12. A sterilization/deodorization means for dissipating electrons into stored liquid in which anaerobic bacteria inhabit, in order to sterilize the said anaerobic bacteria as well as deodorize foul odor, wherein the electron generation means according to any one of claim 1 to claim 4, a ground wire, and an air supply means are included;

the said ground wire electrically grounds the said liquid and the ground as well as while the said air supply means supplies foamed air into the said liquid, the said one terminal is immersed in the said liquid and dissipates electrons;

the liquid with electrons supplied is stirred by the said air, sterilizes the said anaerobic bacteria, and deodorizes the foul odor.

13. The sterilization/deodorization means for sterilizing anaerobic bacteria as well as deodorizing foul odor, wherein the electron generation means according to any one of claim 1 to claim 4, a tank for storing liquid, a spraying means for the said liquid, a ground wire, and an air supply means are included;

the said ground wire electrically grounds the said liquid and the ground as well as while the said air supply means supplies foamed air into the said liquid, the said one terminal is immersed in the said liquid and dissipates electrons and charges the liquid; and the said spraying means sprays the charged said liquid to sterilize and deodorize.

* * * * *